United States Patent [19]
Bailey et al.

[11] Patent Number: 5,607,304
[45] Date of Patent: Mar. 4, 1997

[54] IMPLANT CONNECTOR

[75] Inventors: A. Gregory Bailey, Alabaster; A. C. Folsom, Jr., Pelham, both of Ala.

[73] Assignee: Crystal Medical Technology, a division of Folsom Metal Products, Inc., Birmingham, Ala.

[21] Appl. No.: 422,797

[22] Filed: Apr. 17, 1995

[51] Int. Cl.$^6$ .................................................. A01C 8/00
[52] U.S. Cl. .......................... 433/174; 433/173; 606/73
[58] Field of Search ................................. 433/169, 172, 433/173, 174, 175; 606/65, 73; 411/309, 311, 411, 414, 415, 423, 426, 307, 310; 285/333, 334

[56] References Cited

U.S. PATENT DOCUMENTS

| | | | |
|---|---|---|---|
| 4,150,702 | 4/1979 | Holmes | 411/310 |
| 4,423,893 | 1/1984 | Holmes | 285/334 |

FOREIGN PATENT DOCUMENTS

| | | | |
|---|---|---|---|
| 701556 | 1/1965 | Canada | 411/307 |

*Primary Examiner*—Cary E. O'Connor
*Attorney, Agent, or Firm*—Veal & Associates

[57] ABSTRACT

A threaded connection for medical implants utilizes root and crest interference profile, such that the major and minor diameters of the thread profile on the male and female members of the connection are selected such that the minor diameter of one member is larger than the major diameter of the other, such that an interference condition is created along the helical path of the thread. This interference condition increases the radial stability of the connection and increases the torque required to loosen the connection when made up.

6 Claims, 4 Drawing Sheets

IMPLANT CONNECTOR

This application is related to application Ser. No. 08/387320, pending.

FIELD OF THE INVENTION

The present invention relates to prosthetic implantation of devices which are osseointegrated into bone. In more particularity, the present invention relates to the field of connectors used in such implants that secure the prosthesis to the implanted portion of the device. The present invention relates to the design of the thread profile so as to maximize the effectiveness of the connection within the implant/prosthesis assembly.

BACKGROUND

The prior art of implants extends back, at least, into the last century; however, only in the last twenty-five years have implants such as hip replacements, knee replacements and dental implants been widely used. These devices often employ threaded connections to fasten components of the prosthetic assembly together. Reported common problems noted by practitioners are breakage of the screw and loosening of the screw fixating the prosthesis in U.S. Pat. No. 5,213,500, for example. It is believed that one cause of the failure of the threaded connection is the stress imposed on selected threads along the connection. On conventional straight V-threads, this thread is the last engaged thread closest in proximity to the head of the screw or bolt. A nominally manufactured component can place portions of the threads in stress conditions above the yield strength of the material, resulting in permanent deformation of the thread. This yielding may lead to a loss of preload tension and retained torque in the connection, leading to relative motion between the joined components, and compromising the function of the prosthesis. Likewise, dynamic fatigue of the overloaded fastener can lead to catastrophic failure. These stress concentrations are compounded by the physical size restraints placed on prosthetic components. The materials which are available to the designer to choose from, to wit, —polymers, metals, and composites—oftentimes exhibit creep characteristics. The stress-raising factors encountered in implants aggravate the tendency of these materials to have time-dependent strain at stress levels below yield.

SUMMARY OF THE INVENTION

It is an object of the present invention to provide a threaded connector for use in medical implants which is resistant to loss of torque due to "backing off".

Another object of the invention is to provide a threaded connector for use in medical implants which enhances radial stability of the connector.

The ultimate object of the invention is to provide a medical implant connector which provides improved fixation of the implant during the life of the patient.

These and other objects and advantages of our implant connector are achieved in our unique formation of the thread of the connector such that the connector male and female portions have interfering cooperative diameters. That is to say, the root of the male member has a diameter greater than the crest of the female member. Since the male root and female crest attempt to occupy the same space, an interference condition is created such that the metal to metal deformation occurs, resulting in a secure seal and increased resistance to decoupling through friction along a helical path defined by the interference. Depending on the malleability and rigidity of the material used the interference condition may be limited to one interface or may be utilized along multiple interfaces; for example, at the major and/or minor diameters of the thread.

BRIEF DESCRIPTION OF THE DRAWINGS

Apparatus embodying features of our invention are depicted in the accompanying drawings which form a portion of this disclosure and wherein.

DESCRIPTION OF THE PREFERRED EMBODIMENT

Figure 1:
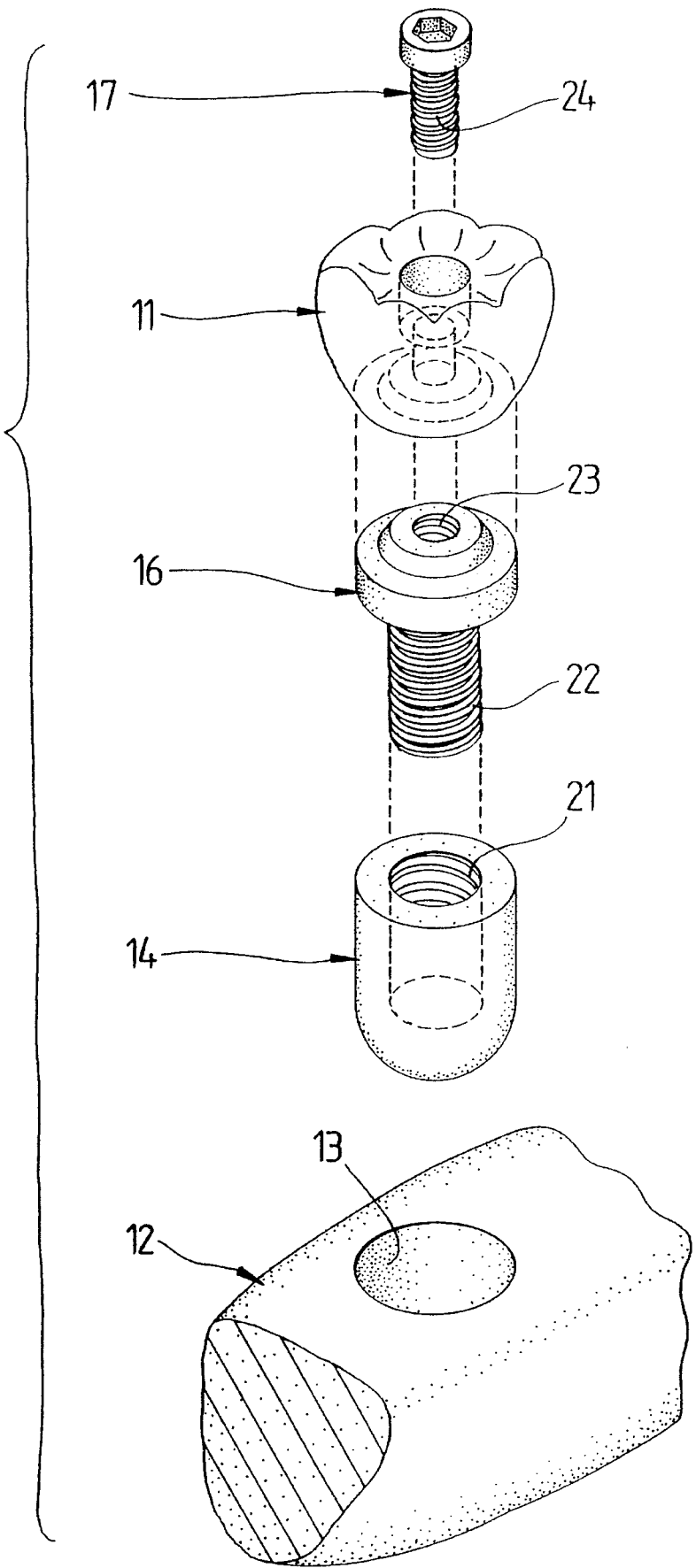
FIG. 1 is an exploded perspective view, partially in section, showing the component parts of a dental implant.

Referring to the drawings for a clearer understanding of the invention, it may be seen in FIG. 1 that the invention is adapted for use in the field of dental implants, wherein a prosthesis, such as a tooth 11 or bridge (not shown), is to be attached to the underlying bone 12. As will be appreciated from the prior art, the surgeon prepares a socket 13 in the bone 12 and positions the implant fixture 14 within the bone 12. The present invention is not directed to the attachment of the fixture 14 to the bone 12; therefore, the external configuration, as shown, is not intended to depict any particular implant fixture. However, the invention is directed to the interaction of the implant 14 with an abutment 16 received therein, and the interaction of the abutment 16 with a screw 17 used to attach the prosthesis 11 to the abutment 16.

Figure 2:
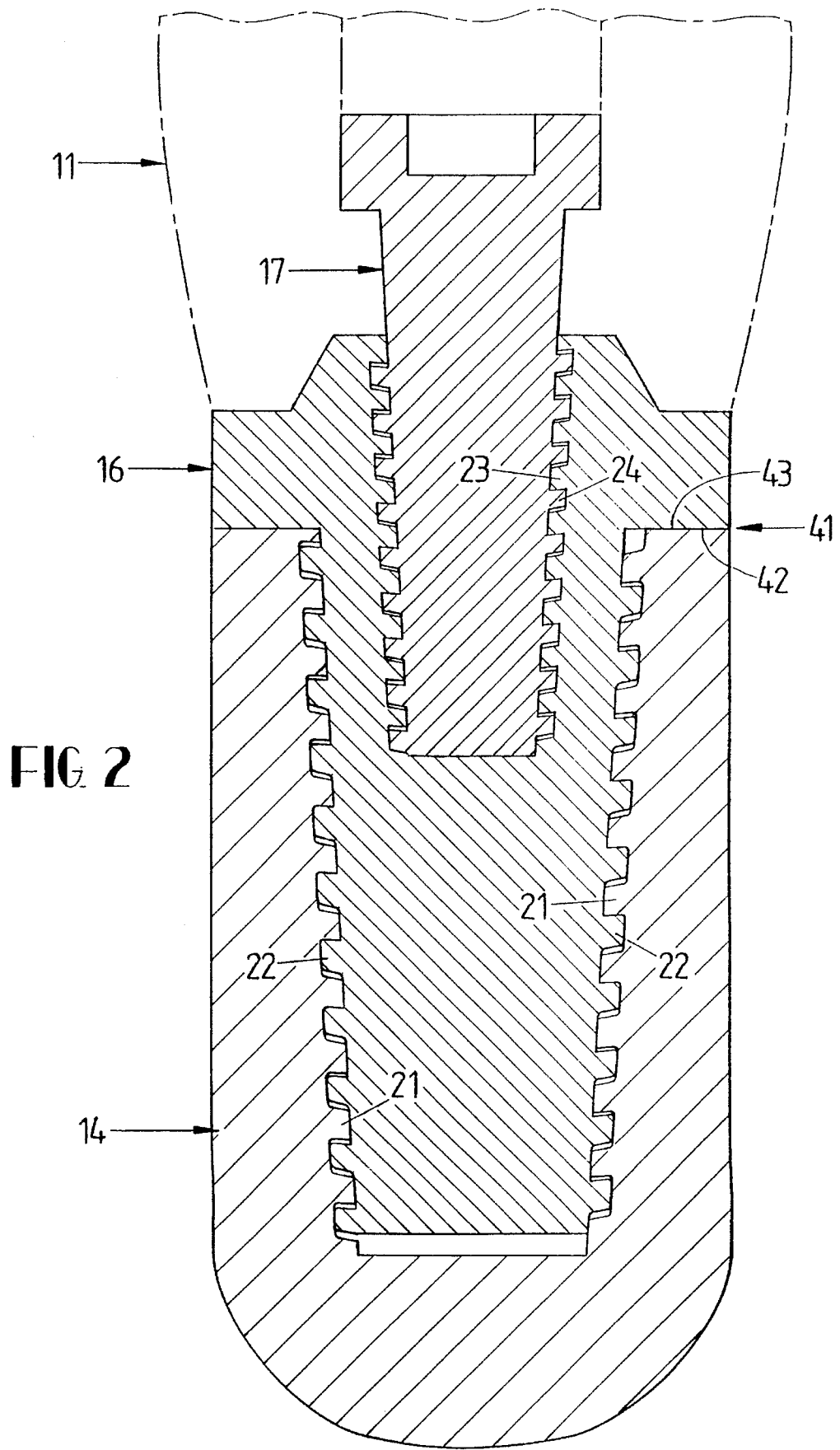
FIG. 2 is a sectional view of the implant assembly along the longitudinal axis.
Figure 3:
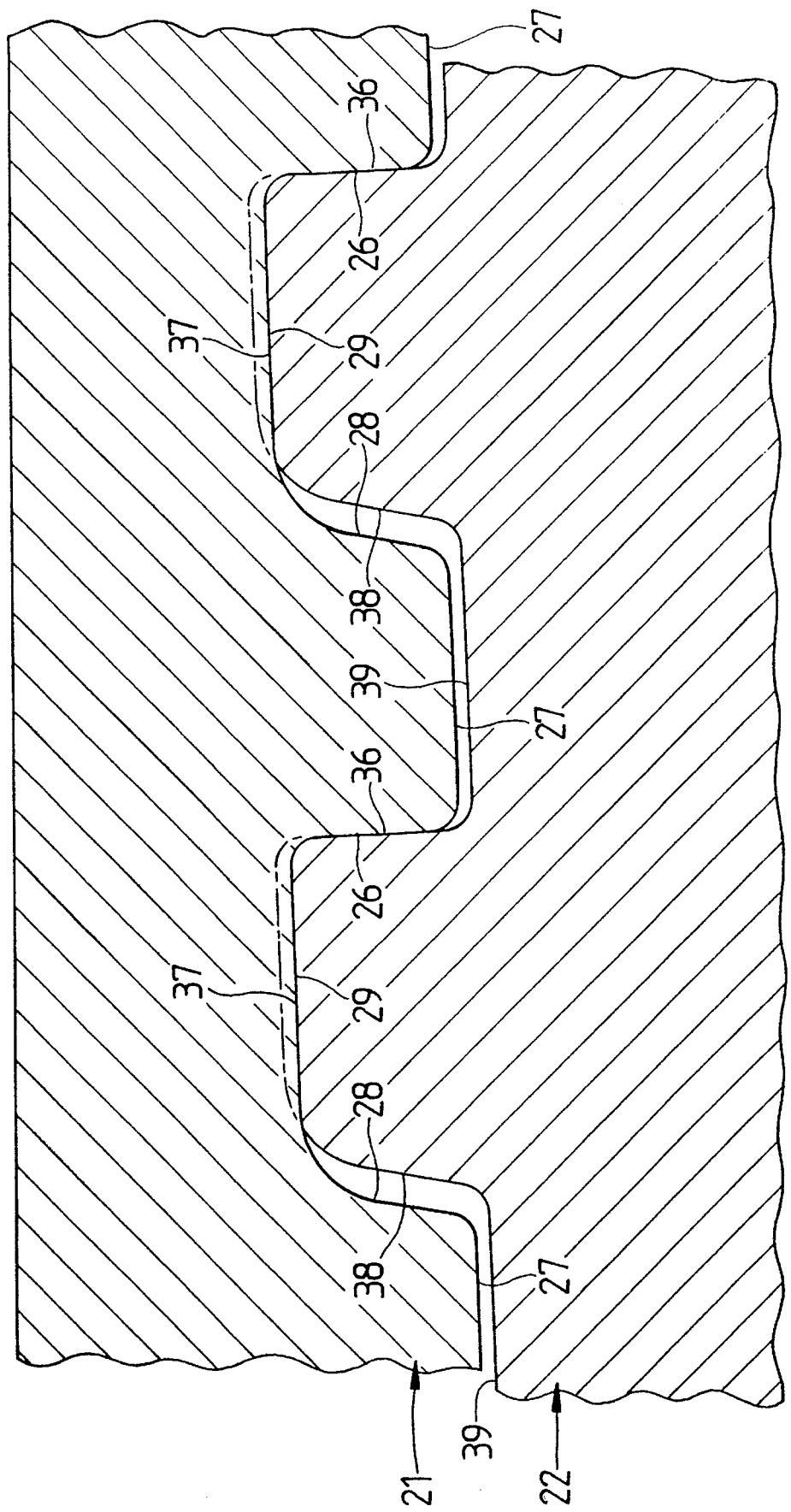
FIG. 3 is a sectional view showing the thread profile of the connection wherein the root and crest surface interfere when the connection is made up.
Figure 4:
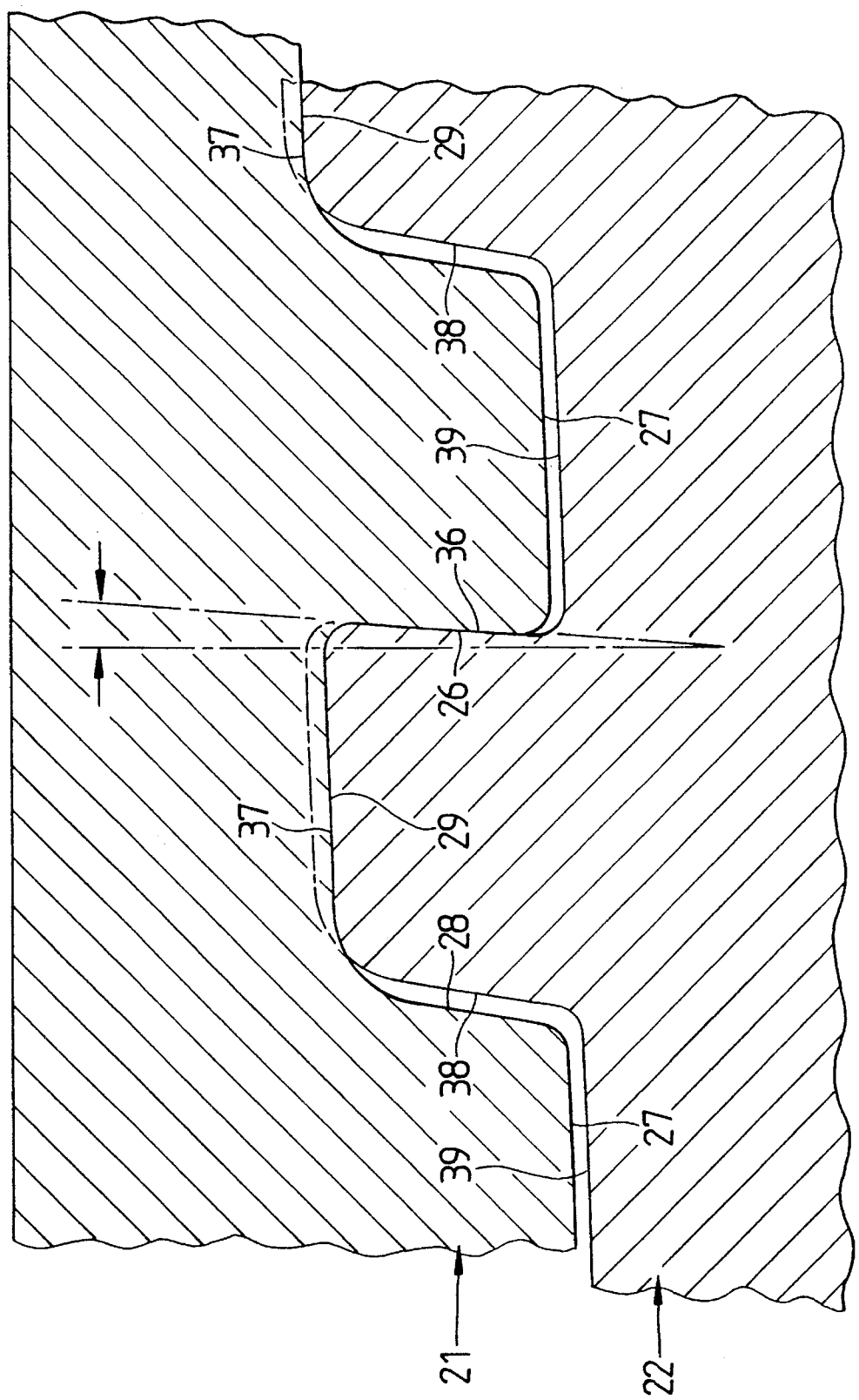
FIG. 4 is a sectional view showing an alternate thread profile of the connection having a negatively inclined load flank, wherein the root and crest surface interfere when the connection is made up.

As may be seen more clearly in FIGS. 2–4, the present invention is directed specifically to the formation and the interaction of the threaded connection between the components.

Implant 14 has a female thread 21 which cooperatively engages the male thread 22 of the abutment 16. Likewise, abutment 16 has a threaded axial bore wherein female threads 23 are positioned to engage the male thread 24 of screw 17. It will be noted that the profile of the thread is a modified truncated thread, wherein the female thread profile includes a load flank 26 intersecting a crest 27, a stab flank 28 extending from the crest 27 to a root 29, such that the turns of the thread, hereinafter referred to as the threads, along the length of the fastener sequentially repeat the profile, with the crest defining the minor or inner diameter of the thread and the root the major or outer diameter. Likewise, the male thread profile includes a load flank 36 intersecting a crest 37, and a stab flank 38 extending from the crest 37 to a root 39, such that the threads along the length of the fastener sequentially repeat the profile, with the crest defining the major or outer diameter of the thread and the root the minor or inner diameter. These two interfaces provide surface to surface contact to distribute bearing stresses. The thrust connection 41 is usually the abutting portion of the connector which prevents further longitudinal relative movement of the connector components. For example, the abutment 16 may have a shoulder 42 which is urged into contact with the implant surface 43. It will be appreciated that tightening the connector loads the connection by placing the screw, or bolt, under tension between the thrust connection and the load flank interface. If the male thread profile and female thread profile are not properly matched, the connection will not remain secure. Further, dynamic loading, such as by chewing in a dental implant or movement in an orthopedic implant, will also load the connector.

The present invention is specifically directed to the interference at the crest and root of the connection. By selectively choosing diameters for the male and female connectors which result in root to crest interference a connection can be made which requires greater torque to loosen than a connection which has no such interference. Also, such a connection is less susceptible to motion between the components. As may be seen in FIG. 3, the root 29 of the female member may be in interference with the crest 37 of the male member or, although not depicted, the root 39 of the male member may be in interference with the crest 27 of the female member, or all four surfaces may be in root to crest interference. It should be understood that the deformation of the metal at such interferences forms a superior seal and bond therebetween; thus, the materials of the thread and the depth of interference should be selected to allow the connection to be fully made up with the interference along a helical path. It is also preferable for the thread to be on a taper to reduce helical distance to be traversed under full interference to reduce propensity to gall.

The disclosure of copending application Ser. No. 08/387320 is incorporated herein by reference. As described therein, a connection may be enhanced by varying the lead of one of the threaded members. The present invention may be employed in a variable lead connection to further enhance the stability of the connection, such that interference is generated at the load flank abutment as well as at the root crest abutment. Likewise, the thread may be formed with a negatively inclined load flank as in FIG. 4, and as more fully disclosed in another of our copending applications, and such a thread may be enhanced through the use of selective root to crest interference.

Referring particularly to FIG. 4, it may be seen that the female receptacle utilizing our invention has a negative load flank 26, such that the load flank adjacent the crest of the thread is closer to the thrust connection 41 than the same load flank 26 adjacent the root of the thread. The male thread load flank 36 is complementary. Thus, at the minor diameter of abutting load flanks 26 and 36 when made up under pre-load stress, a plane normal to the connection axis passes through the male thread 22, such that a portion of the material forming the thread radially overlies the female load flank. Accordingly, radial outward movement of the female thread would require displacement of the interstitial portion of the male thread in the angle between the female load flank and root, such that an interference condition would occur. It may be seen that the forces required to overcome the interference will be dictated by the malleability of the material selected and the volume of material involved, such that this type thread profile significantly increases the resistance of the connection to radial relative motion.

While we have shown our invention in various forms, it will be obvious to those skilled in the art that it is not so limited but is susceptible of various changes and modifications without departing from the spirit thereof.

What we claim is:

1. An implant assembly for use in a medical implant, including an implant provided with an abutment for attachment to a prosthesis by a threaded fastener, said abutment and said implant having a cooperative male and female thread and a thrust connection between connected parts, wherein said male and female threads have cooperative oppositely disposed major and minor diameter portions forming their respective root and crests, and wherein the improvement comprises: a major diameter portion of one of said male and female threads sized such that it creates interference with the cooperative oppositely disposed minor diameter portion of said other thread when the connection is made up.

2. A medical implant assembly having an improved threaded connection for use in implant connectors, wherein an implant is provided with an abutment for attachment to a prosthesis by a threaded fastener, wherein said abutment, said implant, and said fastener each have a cooperative male and female thread and a thrust connection therebetween, wherein the improvement comprises: a major diameter portion of one of said male and female threads sized such that it creates interference with a cooperative oppositely disposed minor diameter portion of said other thread when the connection is made up.

3. An implant assembly for use in a medical implant, including an implant provided with an abutment for attachment to a prosthesis by a threaded fastener, wherein said abutment, said implant, and said fastener each have a cooperative male and female thread and a thrust connection therebetween, wherein the improvement comprises: a major diameter portion of one of said male and female threads sized such that it creates interference with the cooperative oppositely disposed minor diameter portion of said other threads when the connection is made up.

4. A medical implant assembly having an improved thread profile for use in implant connectors, wherein a threaded member is used to attach components of the implant and is threadably engaged by a cooperatively formed threaded receptacle, said thread profile including a stab flank and a load flank separated by a crest with successive turns of said thread about a longitudinal axis being separated by a root, wherein a major diameter portion of said threaded member is sized such that it creates interference with a cooperative oppositely disposed minor diameter portion of said threaded receptacle when the connection is made up.

5. An improvement in medical implant connections, wherein an implant assembly uses an implant secured within a cavity formed within a bone of a patient, said implant forming a threaded receptacle, an abutment having an external thread cooperatively formed for engagement with said implant and an internal thread, a fastener having an external thread cooperatively formed for engagement with the internal thread of said abutment for fastening a prosthesis to said abutment, wherein the improvement comprises a thread profile for at least one set of cooperatively formed threads comprising a stab flank and load flank separated by a crest, wherein successive turns of said thread along a longitudinal axis are separated by a root, and wherein a root of one of said male and female threads is sized such that it creates interference with a cooperative oppositely disposed crest of said other thread when the connection is made up.

6. An improvement in dental and orthopedic implant connections, wherein an implant has at least two members held in abutment by a threaded union, each member having a cooperative thread profile including a load flank and stab flank separated by a crest with the thread forming turns about a longitudinal axis through said union, forming a root between the adjacent stab and load flanks, a major diameter portion of one of said members sized such that it creates interference with a cooperative oppositely disposed minor diameter portion of said other member when the connection is made up.

* * * * *